United States Patent [19]

Nakayama

[11] Patent Number: 5,330,913
[45] Date of Patent: Jul. 19, 1994

[54] METHOD OF DISRUPTING THE CHLORELLA CELL WALL BY CELL RUPTURE

[76] Inventor: Hideo Nakayama, Daiichi Sun Chlorella Building 868, Monzencho, Hanayamachi-dori, Horikawa Nishiiru Shimogyo-ku, Kyoto-shi 600, Japan

[21] Appl. No.: 939,264

[22] Filed: Sep. 2, 1992

[30] Foreign Application Priority Data

Sep. 11, 1991 [JP] Japan .................. 3-261156

[51] Int. Cl.$^5$ .................................... C12N 1/06
[52] U.S. Cl. ...................... 435/259; 435/29; 435/243; 435/316; 435/803
[58] Field of Search ............... 435/29, 243, 259, 310, 435/316, 803; 436/63, 177

[56] References Cited

U.S. PATENT DOCUMENTS 4,464,295  8/1984  Bhaduri et al. ............... 530/419
4,983,523  1/1991  Li et al. ........................ 435/259 X

FOREIGN PATENT DOCUMENTS 0303791  6/1988  European Pat. Off. .
2918212  11/1980  Fed. Rep. of Germany .
58-126782  7/1983  Japan .
62-236478  10/1987  Japan .

OTHER PUBLICATIONS

Brock et al. Biology of Microorganisms-5th edition, pp. 9, 16 and 82-83, 1988.
Lamanna et al. (Journal unknown)-1959, pp. 104-109.
Reháček et al. Applied Microbiology, vol. 17, No. 3, Mar. 1969, pp. 462-466.
Dictionary of Microbiology and Molecular Biology-2nd edition, Singleton et al., 1987, pp. 178-179, 371-372 and 964.

Primary Examiner—James C. Housel
Assistant Examiner—Maureen M. Wallenhorst
Attorney, Agent, or Firm—Vineet Kohli

[57] ABSTRACT

The CHLORELLA cell wall is disrupted by forming partially high- and low-pressure portions at high density in an aqueous suspension of CHLORELLA cells, instantaneously shifting the CHLORELLA cells in the aqueous suspension from a high-pressure state to a low-pressure state by interaction of the movement, dissipation and growth of these high- and low-pressure portions and the flowing of the aqueous suspension, and rupturing the CHLORELLA cells by their rapid expansion upon the shift.

1 Claim, 2 Drawing Sheets

METHOD OF DISRUPTING THE CHLORELLA CELL WALL BY CELL RUPTURE

BACKGROUND OF THE INVENTION

1. Field of the Invention The present invention relates to a method of disrupting the CHLORELLA cell wall by rupturing CHLORELLA cells.

2. Description of the Prior Art

CHLORELLA contains more than about 50% (w/w) high quality protein with an excellent essential amino acid composition and is rich in nutrients, such as various vitamins. In addition, it exhibits high proliferating capability under solar light. To efficiently utilize CHLORELLA as a food, its cell wall is disrupted to increase its digestion and absorption rate.

Although the cell wall may be disrupted by milling, disruption efficiency achieved by such milling is subject to limitation.

The object of the present invention is to provide a method of efficiently disrupting the CHLORELLA cell wall on the basis of non-milling disruption.

SUMMARY OF THE INVENTION

The method of disrupting the CHLORELLA cell wall by cell rupture according to the present invention is characterized in that partially high- and low-pressure portions are formed at high density in an aqueous suspension of CHLORELLA cells, the CHLORELLA cells in the aqueous suspension are instantaneously shifted from a high-pressure state to a low-pressure state by interaction of the movement, dissipation and growth of the high- and low-pressure portions and the flowing of said aqueous suspension, and the CHLORELLA cells are ruptured by their rapid expansion upon said shift.

According to the method of the present invention, the CHLORELLA cells in the aqueous suspension undergo an instantaneous shift from a high-pressure state to a low-pressure state uniformly with the lapse of time by interaction of the movement, dissipation and growth of the high- and low-pressure portions and the flowing of said aqueous suspension, and the CHLORELLA cell wall is uniformly and efficiently disrupted by cell rupture.

Figure 1:
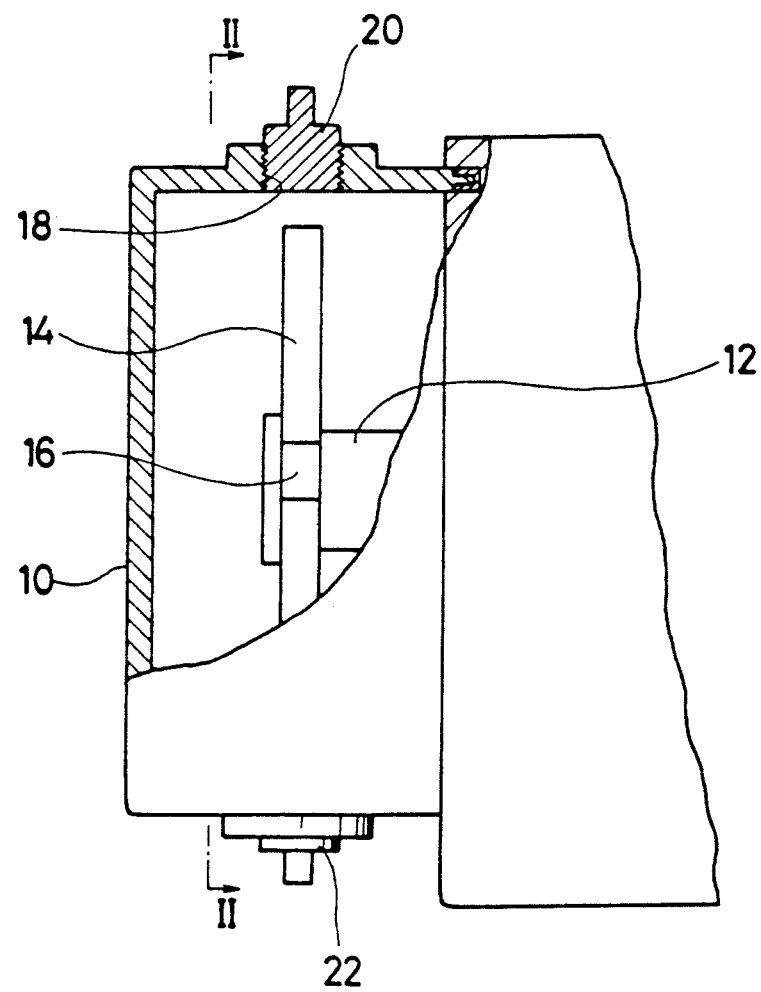
FIG. 1 is a cross-sectional view of a cylindrical tight-sealable container used in the instant invention.
Figure 2:
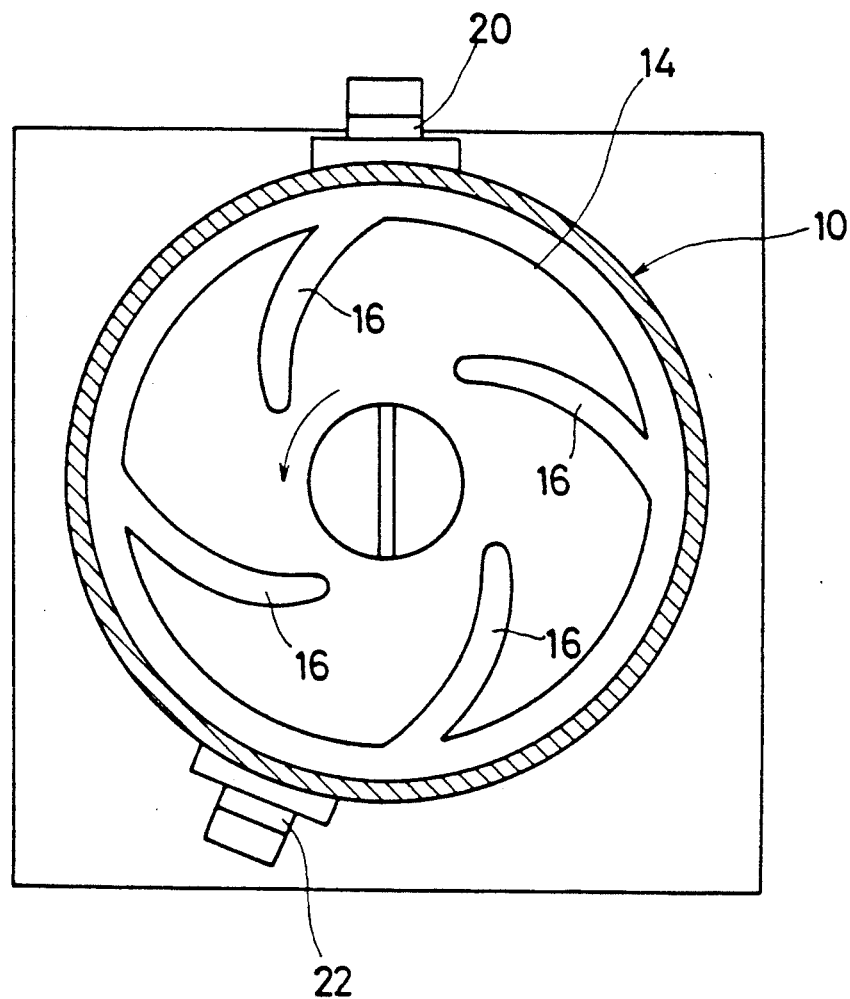
FIG. 2 is a cross-sectional view as viewed on the II—II line of FIG. 1.

In these figures, the numerical symbols denote the following: 10, a tight-sealed container; 12, a rotation shaft; 14, an impeller blade.

DETAILED DESCRIPTION OF THE INVENTION

When partially high- and low-pressure portions formed at high density in an aqueous suspension of CHLORELLA cells and shifted, dissipated and grown, while said aqueous suspension is flowed, the CHLORELLA cells in the aqueous suspension are instantaneously shifted from a high-pressure state to a low-pressure state by interaction thereof.

By rapid expansion upon said shift, the CHLORELLA cells are ruptured, and the CHLORELLA cell wall is disrupted.

The CHLORELLA cells in the aqueous suspension undergo an instantaneous shift from a high-pressure state to a low-pressure state uniformly with the lapse of time by interaction of the movement, dissipation and growth of the high- and low-pressure portions and the flowing of said aqueous suspension. Thus, the cell wall of the CHLORELLA cells in the aqueous suspension are uniformly and efficiently disrupted.

Examples of more specific embodiment of the method of disrupting the CHLORELLA cell wall by cell rupture described above are given below.

In a preferred embodiment of the method of disrupting the CHLORELLA cell wall by cell rupture, rigid spheres having a constant diameter of 500 to 800 $\mu$m are placed in a cylindrical tight-sealed container having an impeller blade therein in an amount equivalent to 80 to 85% of the capacity of the tight-sealed container, an aqueous suspension of not more than 30% by dry weight CHLORELLA cells is added to the tight-sealed container in an amount nearly equivalent to the remaining parts of the capacity of the tight-sealed container, said impeller blade is rotated at a peripheral speed of 10 to 20 m/s to form partially high- and low-pressure portions at high density in said aqueous suspension in spaces among the rigid spheres being stirred, the CHLORELLA cells in the aqueous suspension are instantaneously shifted from a high-pressure state to a low-pressure state by interaction of the movement, dissipation and growth of these high- and low-pressure portions and the flowing of said aqueous suspension, and the CHLORELLA cells are ruptured by their rapid expansion upon said shift.

In another preferred embodiment of the method of disrupting the CHLORELLA cell wall by cell rupture, rigid spheres 70 to 80% of which have a diameter of about 500 $\mu$m and the remaining parts of which have a diameter of about 800 $\mu$m are placed in a cylindrical tight-sealed container having an impeller blade therein in an amount equivalent to 80 to 85% of the capacity of said tight-sealed container, an aqueous suspension of not more than 30% by dry weight CHLORELLA cells is added to the tight-sealed container in an amount nearly equivalent to the remaining parts of the capacity of the tight-sealed container, said impeller blade is rotated at a peripheral speed of 10 to 20 m/s to form partially high- and low-pressure portions at high density in said aqueous suspension in spaces among the rigid spheres being stirred, the CHLORELLA cells in the aqueous suspension are instantaneously shifted from a high-pressure state to a low-pressure state by interaction of the movement, dissipation and growth of these high- and low-pressure portions-and the flowing of said aqueous suspension, and the CHLORELLA cells are ruptured by their rapid expansion upon said shift.

Preferably, the impeller blade used in these methods is of the disk type having notches, since it is suitable for high-speed rotation and offers the highest possible stirring efficiency. Any material, including metal and synthetic resin, can be used for the impeller blade, as long as it is sufficiently strong and rigid.

From the viewpoint of generally efficient stirring of the rigid spheres and suspension in the tight-sealed container, it is preferable to set the impeller blade so that its rotation axis is aligned on the axis of the cylindrical tight-sealed container, and that the maximum diameter of the impeller blade is about 80 to 90% of the inside diameter of the tight-sealed container.

Also, it is desirable that the total thickness of the one or more impeller blades set in the tight-sealed container be about 15 to 25% of the inside length of the tight-sealed container, and that the number of impeller blades be increased according to the inside length of the tight-sealed container to ensure a uniform stirring effect.

Examples of rigid spheres which can be used in the above methods include ceramic balls and glass balls.

When 70 to 80% by number of the rigid spheres contained in the tight-sealed container have a diameter of about 500 μm and the remaining parts have a diameter of about 800 μm, the pressure difference between the partially high- and low-pressure portions increases so that the CHLORELLA cell wall is more efficiently disrupted.

The reason why the ratio of CHLORELLA cells in the aqueous suspension is set at not more than 30% by dry weight is that if the ratio exceeds 30% by weight, it will be impossible to form partially high- and low-pressure portions at a sufficient density to efficiently disrupt the cells. From the viewpoint of operating efficiency, the ratio of CHLORELLA cells in the aqueous suspension is desirably at least 5% by dry weight.

EXAMPLES

The present invention is hereinafter described in more detail by means of the following examples, which are not to be construed as limitative.

EXAMPLE 1

As illustrated in FIG. 1, in a cylindrical tight-sealed container 10 having an inside diameter of 80 mm and an inside length of 40 mm, a rotation shaft 12 is provided concentrically with the axis of tight-sealed container 10. To rotation shaft 12, an impeller blade 14 is fixed concentrically therewith at the central portion with respect to the longitudinal direction of tight-sealed container 10.

This rotation shaft 12 is rotated by known rotating means such as a motor, a driving pulley, a transmission belt and a driven pulley. Also, impeller blade 14 is a metal disc having a diameter of 70 mm and a thickness of 5 mm, and is rotationally symmetrically equipped with four units of radially outwardly convex circular notch 16 from the outer periphery in the rotationally inward direction.

18 is an inlet for introducing the glass balls (rigid spheres), the aqueous suspension of CHLORELLA cells, etc. into tight-sealed container 10. 20 is a plug for stopping inlet 18. 22 is a plug for stopping the outlet.

Tight-sealed container 10 houses glass balls having a specific gravity of about 2.5 in an amount equivalent to about 85% of the capacity thereof. About 75% by number of the glass balls have a diameter of about 500 μm, and the remaining parts have a diameter of about 800 μm. A suspension in an amount nearly equivalent to the remaining parts of the capacity of tight-sealed container 10 is also contained in tight-sealed container 10. This suspension is an aqueous suspension of 20% by dry weight CHLORELLA cells.

Under the above conditions, the mixture of glass balls and suspension was stirred by rotating rotation shaft 12 so that the peripheral speed of impeller blade 14 was nearly 15 m/s. Such stirring was conducted repeatedly with the stirring time prolonged for 5 seconds in turn. After each stirring, a sample was taken and microscopically observed for cell wall disruption by cell rupture. 150 seconds elapsed until the cell wall was disrupted in almost 95% CHLORELLA cells.

When the ratio of CHLORELLA cells in the suspension was 5% by dry weight, cell wall disruption time was 155 seconds. When the ratio was 30% by dry weight, cell wall disruption time was 165 seconds. When the peripheral speed of impeller blade 14 was changed to 10 m/s and 20 m/s, while keeping the CHLORELLA cell ratio at constantly 20% by weight, a slight decrease and slight increase in efficiency occurred, respectively.

When the CHLORELLA cell ratio was 20% by weight, the peripheral speed of impeller blade 14 was almost 15 m/s and glass balls were placed in tight-sealed container 10 in an amount equivalent to about 80% of the capacity thereof, 155 seconds elapsed until the cell wall was disrupted in almost 95% CHLORELLA cells.

When about 70% by number of the glass balls placed in tight-sealed container 10 in an amount equivalent to about 85% of the capacity thereof had a diameter of about 500 μm and the remaining parts had a diameter of about 800 μm, 150 seconds elapsed until the cell wall was disrupted in almost 95% CHLORELLA cells. When about 80% by number of the glass balls had a diameter of about 500 μm and the remaining parts had a diameter of about 800 μm, 155 seconds elapsed until the cell wall was disrupted in almost 95% CHLORELLA cells.

EXAMPLE 2

In tight-sealed container 10, glass balls having a diameter of about 500 μm and a specific gravity of about 2.5 were placed in an amount equivalent to about 85% of the capacity of tight-sealed container 10. An aqueous suspension of 20% by dry weight CHLORELLA cells was added in an amount nearly equivalent to the remaining parts of the capacity of tight-sealed container 10. Rotation shaft 12 was rotated so that the peripheral speed of impeller blade 14 was nearly 15 m/s, to stir the mixture of glass balls and suspension. Such stirring was conducted repeatedly with the stirring time prolonged for 5 seconds in turn. After each stirring, a sample was taken and microscopically observed for cell wall disruption by cell rupture. 225 seconds elapsed until the cell wall was disrupted in almost 95% CHLORELLA cells.

EXAMPLE 3

Stirring was conducted in the same manner as in Example 2 except that the glass balls had a diameter of about 800 μm. 245 seconds elapsed until the cell wall was disrupted in almost 95% CHLORELLA cells.

COMPARATIVE EXAMPLE 1

Stirring was conducted in the same manner as in Example 2 except that the glass balls were replaced with a mixture (roughly 1:1:1:1) of four sizes of glass ball having diameters of 500 μm, 600 μm, 700 μm and 800 μm, respectively. 370 seconds elapsed until the cell wall was disrupted in almost 95% CHLORELLA cells.

What is claimed is:

1. A method for disrupting CHLORELLA cell walls by cell rupture comprising:
    (a) placing rigid spheres having a diameter of about 500 to about 800 μm in a cylindrical tight-sealable container having a notched impeller blade therein to a volume filling from 80 to 85% of the capacity of the tight-sealable container;

wherein 70 to 80% of said spheres have diameters of about 500 μm and a remainder of said spheres have a diameter of about 800 μm;

said notched impeller blade has a diameter of 80 to 90% of an inside diameter of said cylindrical tight-sealable container;

said notched impeller blade has a thickness of about 15% to about 25% of an inside length of said tight-sealable container;

(b) adding an aqueous suspension of not more than 30% by dry weight CHLORELLA cells to the tight-sealable container in an amount substantially filling the remainder of the capacity of said tight-sealable container;

(c) sealing said tight-sealable container; and (d) rotating said notched impeller blade at a peripheral speed of 10 to 20 m/s.

* * * * *